United States Patent
Schleicher et al.

(10) Patent No.: US 9,383,330 B2
(45) Date of Patent: Jul. 5, 2016

(54) ARRANGEMENT FOR DETERMINING THE PHASE DISTRIBUTION IN MULTIPHASE MEDIA HAVING AT LEAST ONE HIGHLY CONDUCTIVE PHASE

(71) Applicant: Helmholtz-Zentrum Dresden—Rossendorf E.V., Dresden (DE)

(72) Inventors: Eckhard Schleicher, Dresden (DE); Martin Loschau, Bautzen (DE); Laurens Van Campen, Delft (NL)

(73) Assignee: HELMHOLTZ-ZENTRUM DRESDEN—ROSSENDORF E.V., Dresden (DE)

( * ) Notice: Subject to any disclaimer, the term of this patent is extended or adjusted under 35 U.S.C. 154(b) by 0 days.

(21) Appl. No.: 14/771,070

(22) PCT Filed: Feb. 28, 2014

(86) PCT No.: PCT/EP2014/053940
§ 371 (c)(1),
(2) Date: Aug. 27, 2015

(87) PCT Pub. No.: WO2014/131885
PCT Pub. Date: Sep. 4, 2014

(65) Prior Publication Data
US 2016/0011136 A1     Jan. 14, 2016

(30) Foreign Application Priority Data
Feb. 28, 2013  (DE) .......................... 10 2013 203 437

(51) Int. Cl.
| | | |
|---|---|---|
| *G01R 27/26* | (2006.01) | |
| *G01N 27/22* | (2006.01) | |
| *G01N 33/28* | (2006.01) | |
| *G01F 1/66* | (2006.01) | |
| *G01F 1/74* | (2006.01) | |
| *G01N 27/07* | (2006.01) | |
| *G01N 27/08* | (2006.01) | |

(52) U.S. Cl.
CPC ............ *G01N 27/223* (2013.01); *G01N 27/226* (2013.01); *G01N 33/2823* (2013.01); *G01F 1/662* (2013.01); *G01F 1/74* (2013.01); *G01N 27/07* (2013.01); *G01N 27/08* (2013.01)

(58) Field of Classification Search
CPC ..... G01N 27/07; G01N 27/226; G01N 28/23; G01N 33/442; G01N 27/08; G01F 1/662
USPC ................................ 324/663, 664, 71.1, 453
See application file for complete search history.

(56) References Cited

U.S. PATENT DOCUMENTS

| | | | |
|---|---|---|---|
| 4,644,263 A | 2/1987 | Johnson | |
| 5,210,499 A | 5/1993 | Walsh | |
| 7,940,038 B2 * | 5/2011 | Da Silva | ............ G01N 33/2823 324/663 |

FOREIGN PATENT DOCUMENTS

| | | |
|---|---|---|
| DE | 196 49 011 A1 | 5/1998 |
| DE | 101 36 358 A1 | 2/2002 |
| DE | 10 2005 019 739 B3 | 10/2006 |
| DE | 10 2006 019178 A1 | 11/2007 |
| DE | 10 2007 019 926 B4 | 11/2008 |

OTHER PUBLICATIONS

International Search Report for International Application PCT/EP2014/053940 dated May 6, 2014.

* cited by examiner

*Primary Examiner* — Vincent Q Nguyen
(74) *Attorney, Agent, or Firm* — Heslin Rothenberg Farley & Mesiti P.C.

(57) ABSTRACT

A grid sensor for measuring the phase distribution of a multiphase substance mixture with gaseous and liquid components in the presence of a highly conductive phase (such as salt water or liquid metal) employs 3 superposed electrode planes and an electronic measuring device. Application areas include determination of the liquid distribution and the fill level in containers, as well as the investigation of gas-liquid multiphase flows, in particular in pipelines, e.g. in petroleum production and processing.

10 Claims, 3 Drawing Sheets

ARRANGEMENT FOR DETERMINING THE PHASE DISTRIBUTION IN MULTIPHASE MEDIA HAVING AT LEAST ONE HIGHLY CONDUCTIVE PHASE

CROSS REFERENCE TO RELATED APPLICATIONS

This application is a national stage filing under section 371 of International Application No. PCT/EP2014/053940, filed on Feb. 28, 2014, and published in German on Sep. 4, 2014, as WO2014/131885 A1 and claims priority of German application 10 2013 203 437.7 filed on Feb. 28, 2013, the entire disclosure of these applications being hereby incorporated herein by reference.

TECHNICAL FIELD

The invention concerns an arrangement for measuring the phase distribution of a multiphase substance mixture with gaseous and liquid components in the presence of a highly conductive phase. In the following, highly conductive phases are defined as media with high conductivity, for example salt water or liquid metals.

Application areas of the present invention are the determination of the liquid distribution and the fill level in containers, for example, as well as the investigation of gas-liquid multiphase flows, in particular in pipelines, e.g. in petroleum production and processing.

STATE OF THE ART

Grid sensors are often used to investigate two-phase flows or liquid distributions in pipelines and containers. U.S. Pat. No. 4,644,263 A, U.S. Pat. No. 5,210,499 A and DE 19 649 011 C2 describe arrangements with which the electric conductivity within a measuring section can be measured with the aid of a grid-type electrode arrangement and associated electronics. In these arrangements, wire-shaped electrodes of an excitation electrode plane of the grid, which are in electrically conductive connection with the medium, are successively charged with a voltage signal. A current signal is acquired on the wire electrodes of a receiver electrode plane of the grid, disposed at a slight distance parallel hereto and rotated by a plane angle. These arrangements are therefore capable of determining the conductivity between the two planes in the intersections of the projections of the electrodes (referred to in the following as "intersections") with a very high measurement frequency.

For a two-phase flow with exactly one conductive phase, for example a gas-water mixture, the phase distribution in the flow cross section can be determined by recording the conductivity distribution. Phase discrimination for similarly well or poorly conductive phases or components of a flow is not directly possible with these arrangements.

DE 10 2007 019 926 B4 describes a grid sensor that, by measuring the complex electrical admittance in the measuring section, is also capable of distinguishing non-conductive components in the measuring section from one another and determining their proportion.

DE 101 36 358 A1 proposes the use of a channel for conductivity measurement of a uniform fluid. Using it to determine the conductivity of mixed fluids is not intended. Use in batch systems is therefore only possible if different, not mixed, fluids flow through the channel in chronological succession.

DE 10 2006 019 178 A1 describes a grid sensor that is suitable for measuring non-conductive components by recording the complex-valued electrical admittance.

DE 10 2005 019 739 B3 describes a grid sensor that can be used with changing temperatures and pressures, in which the wires of the electrode layers are not rigid, but fixed in the sensor body in such a way that they can expand with changes in temperature and/or pressure.

The hitherto known solutions cannot be used for highly conductive media, however, because in such cases the conductivity of at least one component of the flow comes close to the conductivity of the wires of the sensor. All the wires wetted by medium are thus quasi short-circuited, and as a result the individual intersections can no longer be read independently.

X-ray tomography is one alternative for the determination of the complete phase distribution in a measuring plane. In this case, numerous different x-ray paths have to be laboriously reconstructed. X-ray tomography has the advantage that it does not interfere with the process, because it can be disposed outside the process, but protecting staff from radiation requires a lot of effort and is therefore more likely to be rejected in industrial applications.

BRIEF DESCRIPTION OF THE DRAWING FIGURES

DESCRIPTION OF THE INVENTION

Technical Task

Figure 1:
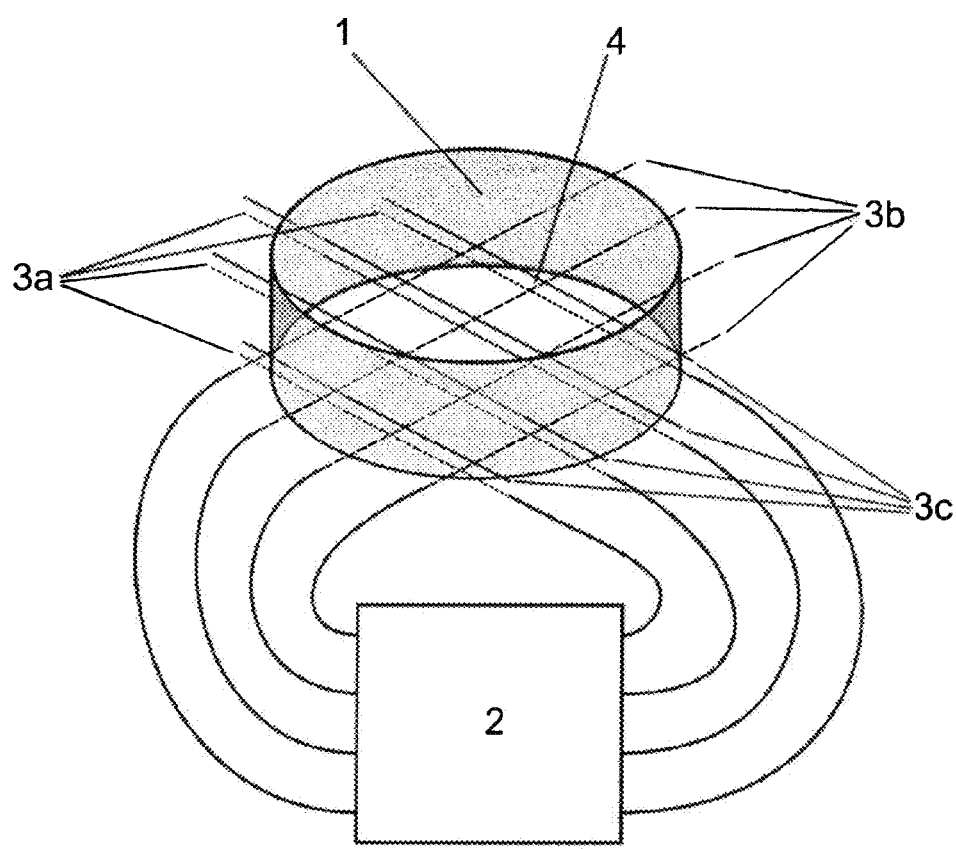
FIG. 1 illustrates an example of an arrangement according to the invention comprising a grid sensor with at least three electrode planes spaced at a small distance from one another, and the associated measurement electronics.

The task of the present invention is to specify an arrangement for the rapid measurement of the phase or component distribution in a flow cross section for substance mixtures with both non-conductive components, e.g. oil or gas, and/or conductive components, as well as highly conductive components, e.g. salt water. Rapid measurements are considered to be measurements with a discrete time difference of less than 1 ms, preferably approx. 100 μs or less.

Technical Solution of the Invention

The measurement of the phase distribution is conducted via the properties that distinguish the different phases. With the exception of point measuring needle probes for local bubble identification, the use of visible light is usually not suitable, because many multiphase flows are not transparent.

The arrangement according to the invention (FIG. 1) comprises a grid sensor (1) with at least three electrode planes spaced at a small distance from one another, and the associated measurement electronics (2). The grid sensor has three levels of wire-shaped electrodes, which are designated as transmitter electrodes (3a), receiver electrodes (3b) and ground electrodes (3c) and are arranged within each plane at a small distance parallel to one another. Exactly one task is thus assigned to each plane.

The orientation of the electrodes of different planes to one another is rotated at an angle in such a way that intersections are formed between the plane of the transmitter electrodes and that of the receiver electrodes. This rotation is preferably orthogonal. The electrical capacitance (or permittivity) of the medium between the transmitter electrodes (3a) and the receiver electrodes (3b) is measured in each individual intersection (4) of the electrode grid. For this purpose (FIG. 2), the transmitter electrodes (3a) and the receiver electrodes (3b) are covered with an electrically insulating layer (5) that makes galvanic isolation from the medium possible, while the ground wires (3c) remain bare to keep the entire fluid at ground potential.

To measure the electrical capacitance (or permittivity) (FIG. 2) of the medium in each intersection (4), the associated transmitter electrode (3a) is charged with AC voltage by means of a frequency generator (6), while all other transmitter electrodes are switched to ground. At the same time, the step response function of the capacitive displacement current flowing through the study medium at the intersection (4) is acquired concurrently on all receiver electrodes (3b) with the aid of a current-voltage converter (7) connected to the receiver electrode, and converted into an equivalent voltage signal. Rectangular or trapezoidal alternating voltages are preferably used as the alternating voltage, because these allow the best evaluation of the measurement results.

Figure 3:
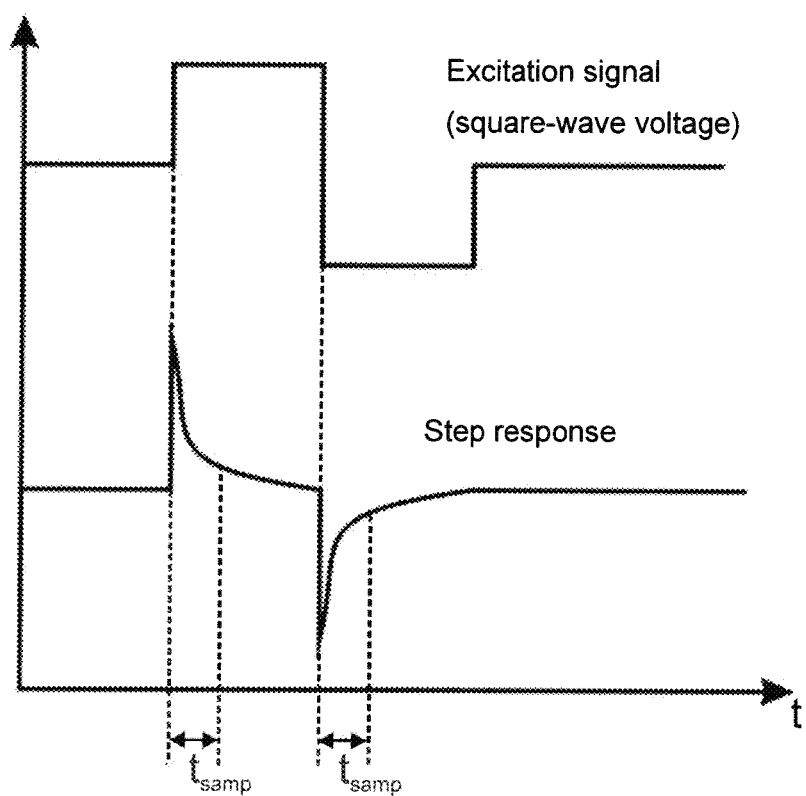
FIG. 3 illustrates the step response of the system on the flank of the excitation signal.

The step response (FIG. 3) of the system on the flank of the excitation signal depends on the gain-bandwidth product of the current-voltage converter (7), the feedback impedance and the electrical permittivity of the medium at the intersection (4). Therefore, at constant gain and geometry conditions, the permittivity at the intersection can be inferred from the step response. For this purpose, at one or more specific points in time $t_{samp}$ after the flank has occurred, the output voltage of the current-voltage converter (7) is digitized by means of an analog-to-digital converter (8) and recorded electronically. A control unit (9), e.g. a microcontroller, is used to synchronize the excitation pulse and the analog-to-digital conversion temporally.

Advantages of the Invention

A novel feature of the invention is the option of a quick two-dimensional measurement of the distribution of non-conductive, as well as conductive and/or highly conductive components in the cross section of a multiphase flow, which, for the first time, allows the measurement of phase fractions and distributions in saltwater oil-gas mixtures.

Applications of the Invention

In industrial facilities currents often consist of more than one phase, such as e.g. in oil production, where flow mixtures of oil, gas, water and sand can occur, in chemical plants, where mixing and separation processes occur, or in the steel industry (molten steel/slag/air). In order to be able to study or verify the mixing or separation of the various phases, these various phases have to be measured and defined.

The relative permittivity generally differs between different media and thus between the phases of a mixture flow. The measuring principle of the grid sensor takes advantage of this physical property to generate two-dimensional images of the phase distribution in the measurement cross section with high spatial and temporal resolution. This method was initially used with a quasi-DC excitation to measure gases in conductive media. For non-conductive media, the dielectric constant can be determined by AC excitation and measurement of the phase shift and the amplitude attenuation.

In media with very low impedance, i.e. high conductivity, the conductivity of which comes close to that of the electrodes in the sensor grid (e.g. salt water), the measurements are distorted by quasi short-circuiting of all the wires in contact with the highly conductive medium if no ground plane is used. The grid sensor with ground plane solves this problem by grounding the entire liquid cross section and isolating the transmitter and receiver wires.

Many applications with multiphase flows contain highly conductive liquids. In the production of petroleum, brine (salt water) is often found and extracted together with oil. The phase distribution in a pipe with oil and salt water can therefore not be determined with a conventional conductivity sensor or with a capacitively measuring grid sensor. The arrangement according to the invention, however, allows the measurement of the phase distribution in such cases.

DESIGN EXAMPLES

The design examples of the invention are described with drawings.

Figure 2:
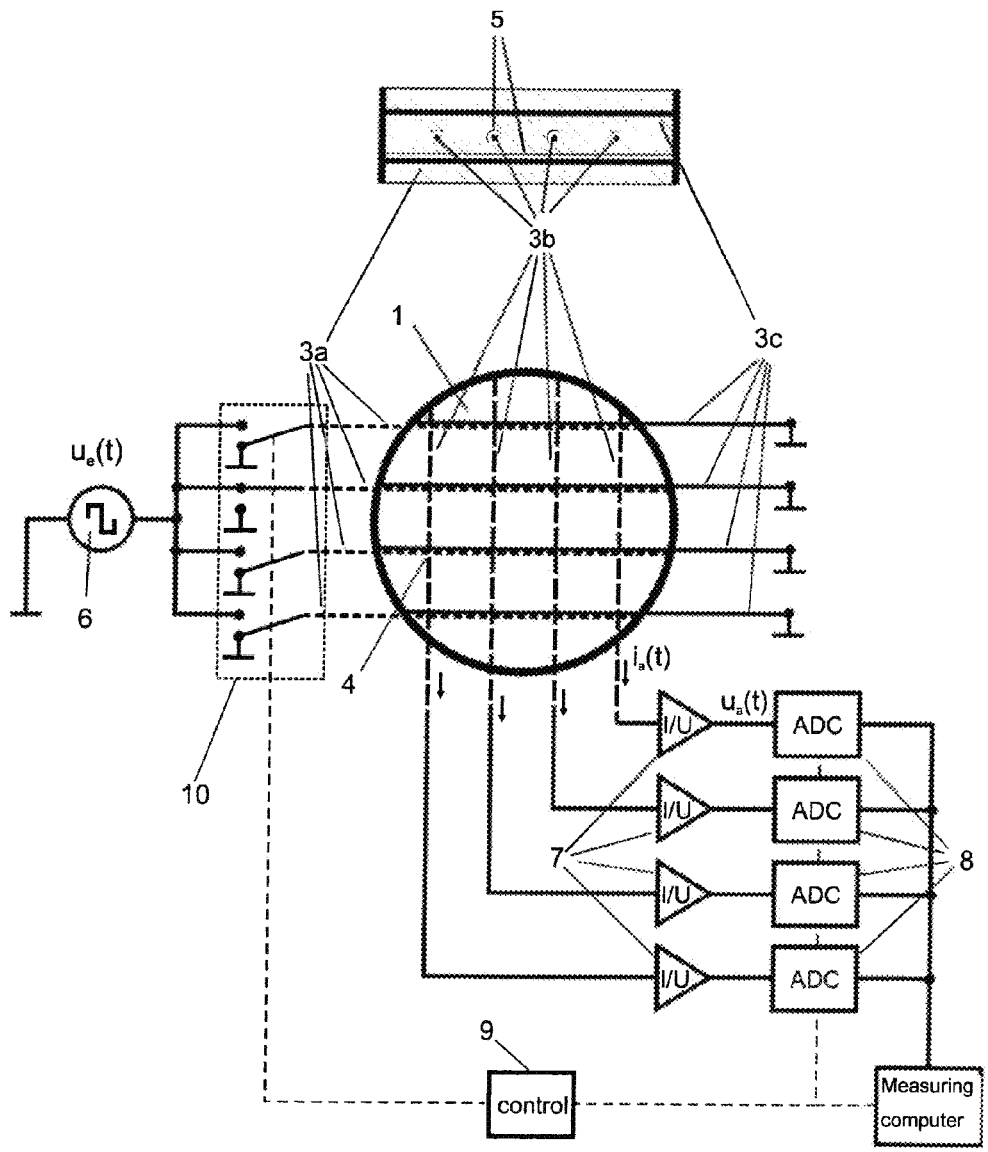
FIG. 2 illustrates in detail an embodiment of the grid sensor with the transmitter electrodes, the receiver electrodes, and the ground electrodes, and the connection of the electrodes to a current-voltage converter.

The drawings FIG. 1, FIG. 2 schematically show, as one design example, grid sensor arrays with 4 transmitter, 4 receiver and 4 ground electrodes and a circular geometry. The grid sensors can also be constructed in other geometries, e.g. rectangular cross sections. Furthermore, the number of electrodes is in theory arbitrary.

The drawing FIG. 1 schematically shows a grid sensor (1) with three electrode planes and the associated measurement electronics (2). The grid sensor has four metal wires per plane (3a—transmitter electrodes, 3b—receiver electrodes, 3c—ground electrodes) that are stretched over the sensor cross section electrically isolated from one another. The anchoring of the wires in the sensor frame is carried out in such a way that each transmitter and receiver electrode is completely electrically isolated from the other electrodes as well as from the frame itself.

On the excitation side, the measurement electronics (FIG. 2) consists of a square-wave generator (6), a multiplexer (10) and a controller (9). The individual transmitter electrodes (3a) of the transmitter plane of the sensor are electrically connected to the outputs of the multiplexer (10). On the receiver side, each of the receiver electrodes (3b) of the receiver plane is connected to a current-voltage converter (7). Analog-to-digital converters (8) are connected to the current-voltage converters (7) to record the step response that, synchronized with the aid of a control unit (9), at a defined time $t_{samp}$ after the excitation flank has occurred, record the current value of the voltage profile at the current-voltage converter (7).

The measurement scheme of the sensor outlined in FIG. 1 and FIG. 2 is as follows: By a controller or microprocessor (9) intended for control, the rectangular or trapezoidal voltage signal of the frequency generator (6) is successively switched to the individual transmitter electrodes (3a) via the multiplexer (10). The multiplexer (10) is designed in such a way that only a single transmitter electrode (3a) is charged by the rectangular or trapezoidal voltage, while all other transmitter electrodes are at zero potential. At the respective active transmitter electrode, a capacitive displacement current flows in the virtual intersections (4) of the wire electrodes to the receiver electrodes (3b) at virtual ground. Due to the insulating layer (5) (e.g. insulating varnish or insulating sleeve), a DC current flow to the transmitter electrodes (3a) and the receiver electrodes (3b) is ruled out. After the voltage jump at the excitation electrode (3a) has occurred, the current flow at the receiver electrode (3b), as a capacitive displacement current, follows the excitation current in the transmitter electrode (3a) with the exponential function $$i(t) = -\frac{U_0}{R_V} \cdot e^{-\frac{t}{\tau}}$$

with $$\tau = R_V \cdot C.$$

Whereby $U_0$ is the amplitude of the excitation voltage, $R_V$ is the series resistance (the sum of the line resistances and wire resistance) and C is the capacitance at the intersection. The capacitance C is, in turn, a function only of the electrical permittivity at the intersection ($\varepsilon_{rel}$) because the geometry of the virtual intersections (4) can be assumed to be constant.

Thus, the following applies:

$$\ln i(t) \sim \frac{1}{\varepsilon_{rel}}.$$

Since the current is linearly converted into an equivalent voltage via the current-voltage converter (7), the measured voltage can also be considered to be indirectly proportional to the dielectric constant of the medium at the intersection. The advantage of the exponential correlation, is that even small changes e.g. air ($\varepsilon_{rel}=1$) and oil ($\varepsilon_{rel}=2$ to 3) are easy to distinguish from one another, even in the presence of water ($\varepsilon_{rel}=80$) without going under in the dynamic range. The present arrangement is also able to determine the relative permittivity $\varepsilon_{rel}$. A skilled person is aware of the fact that a calibration with a known medium, such as water or air, is needed. The geometry factor is determined from this calibration. Consequently, the relative permittivity $\varepsilon_{rel}$ can be determined from the measurement in this way.

The invention claimed is:

1. Arrangement for determination of the phase distribution in multi-phase fluids with at least one highly conductive phase fraction and further presence of non-conductive and/or other conductive components, comprising three superposed electrode planes of wire-shaped electrodes, which are clamped in a sensor frame, wherein:
   a. the electrodes in each plane are disposed in parallel with a small spacing to each other,
   b. two of the electrode planes are galvanically separated from a study medium by an insulating layer and one of the two electrode planes functions as a transmitter plane and another one as a receiver plane, and the two electrode planes are arranged in parallel and rotated at an angle to one other,
   c. a third one of the electrode planes is not isolated and is at ground potential, and the at least one highly conductive phase fraction in contact with the third one of the electrode planes is thus also at ground potential, and
   d. the arrangement is connected to an electronic measuring device configured to measure electrical capacitance or permittivity of the medium in individual intersections formed by the electrodes of the transmitter plane and the electrodes of the receiver plane, and the electronic measuring device is configured to successively charge a corresponding electrode of the transmitter plane with an AC voltage, while all other electrodes of the transmitter plane are switched to ground, and the electronic measuring device is configured to simultaneously measures step response function of a current signal at all electrodes of the transmitter plane in parallel.

2. The arrangement according to claim 1, wherein the orientation of the electrodes of the transmitter plane to the electrodes of the receiver plane is orthogonal.

3. The arrangement according to claim 1, wherein the electrodes of the transmitter and/or receiver plane are coated for insulation with a lacquer or a plastic material or are isolated with an insulating sleeve or insulating tube.

4. The arrangement according to claim 1, wherein the electronic measuring device comprises a frequency generator.

5. The arrangement according to claim 1, wherein the electronic measuring device comprises a multiplexer which successively connects the AC voltage to individual corresponding electrodes of the transmitter plane.

6. The arrangement according to claim 5, wherein the electronic measuring device further comprises a control unit which synchronizes the AC voltage and analog-to-digital conversion.

7. The arrangement according to claim 1, wherein the electronic measuring device comprises a current-voltage converter which is connected to the electrodes of the receiver plane to measure the step response of the current signal and convert the response into an analyzable voltage signal.

8. The arrangement according to claim 7, wherein the electronic measuring device further comprising an analog-digital converter for digitizing the voltage signal.

9. Method for the determination of the phase distribution in multiphase media with the arrangement according to claim 1, comprising consecutively measuring the electric capacitance or permittivity of the medium in each intersection by charging consecutively each corresponding electrode of the transmitter plane with the AC voltage while all other electrodes of the transmitter plane are switched to ground, and, at the same time, measuring the step response function of the current signal in parallel on all electrodes of the receiver plane.

10. The method according to claim 9, wherein the AC voltage comprises a rectangular or trapezoidal AC voltage.

* * * * *